US00PP36111P2

(12) United States Plant Patent
Carr

(10) Patent No.: US PP36,111 P2
(45) Date of Patent: Sep. 17, 2024

(54) APPLE TREE NAMED 'J. Lincoln'

(50) Latin Name: *Malus domestica*
Varietal Denomination: J. Lincoln

(71) Applicant: Jared Carr, Cornish, ME (US)

(72) Inventor: Jared Carr, Cornish, ME (US)

( * ) Notice: Subject to any disclaimer, the term of this patent is extended or adjusted under 35 U.S.C. 154(b) by 0 days.

(21) Appl. No.: 18/445,100

(22) Filed: Apr. 4, 2023

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
See application file for complete search history.

(56) References Cited

U.S. PATENT DOCUMENTS

| | | | |
|---|---|---|---|
| PP34,416 | P2 | 7/2022 | Laymon |
| PP34,437 | P2 | 7/2022 | Dodd et al. |
| PP34,636 | P2 | 10/2022 | Fouillet |

*Primary Examiner* — Susan McCormick Ewoldt
(74) *Attorney, Agent, or Firm* — ArentFox Schiff LLP; Rebecca C. Christon

(57) ABSTRACT

'J. Lincoln' is a new apple tree distinguished by its resistance to the disease fire blight, and its flavorful fruit, which is well-suited for hard cider production.

5 Drawing Sheets

Latin name: The Latin name of the genus and species of the plant claimed is *Malus domestica.*

Variety denomination: Variety denomination: 'J. Lincoln'.

BACKGROUND OF THE VARIETY

'J. Lincoln' is a unique and distinct variety that grew as a chance seedling along the edge of the forest on private family property in Cornish, Maine. The parentage of the 'J. Lincoln' variety is unknown. There is an abandoned orchard nearby where the 'J. Lincoln' variety was discovered, but none of the apples from the abandoned orchard resemble the 'J. Lincoln' variety. Red Astrachan and Duchess of Oldenburg are old varieties that used to be planted in the abandoned orchard, but these varieties lack the tannins that fruit from the claimed 'J. Lincoln' variety possesses. The 'J. Lincoln' apple tree produces fruit that does not resemble fruit from either Red Astrachan or Duchess of Oldenburg varieties. Additionally, fruit from the claimed 'J. Lincoln' variety has tannins that fruit from the Red Astrachan and Duchess of Oldenburg varieties lack. The 'J. Lincoln' apple tree variety was discovered in 2015. 'J. Lincoln' was first asexually propagated by grafting in Cornish, Maine. Since grafting, 'J. Lincoln' has been observed to remain true to type through asexual propagation. The 'J. Lincoln' variety has, over a period of several years, consistently exhibited excellent tree growth habit, precocity, superior fruit quality, and disease resistance.

BRIEF DESCRIPTION OF THE VARIETY

The 'J. Lincoln' apple tree is distinguished by its resistance to the disease fire blight. Fire blight is a contagious disease affecting apples and some other types of fruiting trees. Fire blight is caused by the bacterium *Erwinia amylovora.* The disease is a serious concern to apple producers, as under some conditions fire blight can destroy an entire orchard in a single growing season. The 'J. Lincoln' variety exhibits resistance to fire blight, making it more preferable than other non-resistant varieties. Additionally, the fruit of the 'J. Lincoln' apple tree variety is quite flavorful and well-suited to the production of hard cider. The productivity, storability, and pollination requirements of the 'J. Lincoln' variety are unknown.

Apples from the variety 'J. Lincoln' are also distinguished by attractive flushes of deep red striping overlay on a lighter red-orange base color with caramel colored russet that distends from the stem. 'J. Lincoln' has a growth habit that produces many lateral branches with lots of fruiting spurs. 'J. Lincoln' naturally has a semi-dwarfing growth habit.

BRIEF DESCRIPTION OF THE DRAWINGS

The accompanying photographs show typical specimens of the new variety as depicted in color as nearly true as is reasonably possible. The photographs of the 'J. Lincoln' variety were taken in the years 2021 and 2023 in Cornish, Maine.

DETAILED BOTANICAL DESCRIPTION

Figure 1:
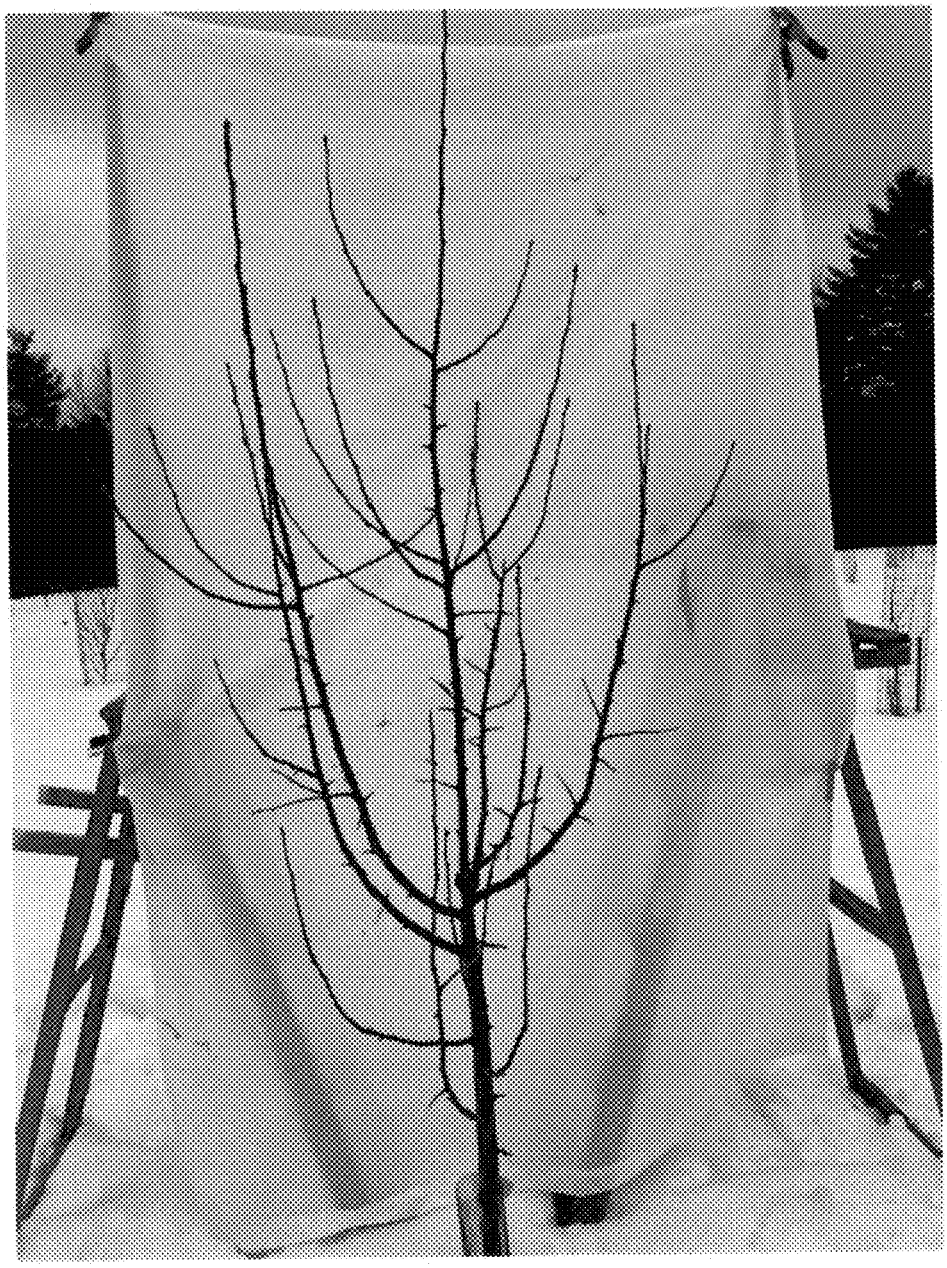
FIG. 1 is a photograph of a 'J. Lincoln' apple tree in winter.
Figure 2:
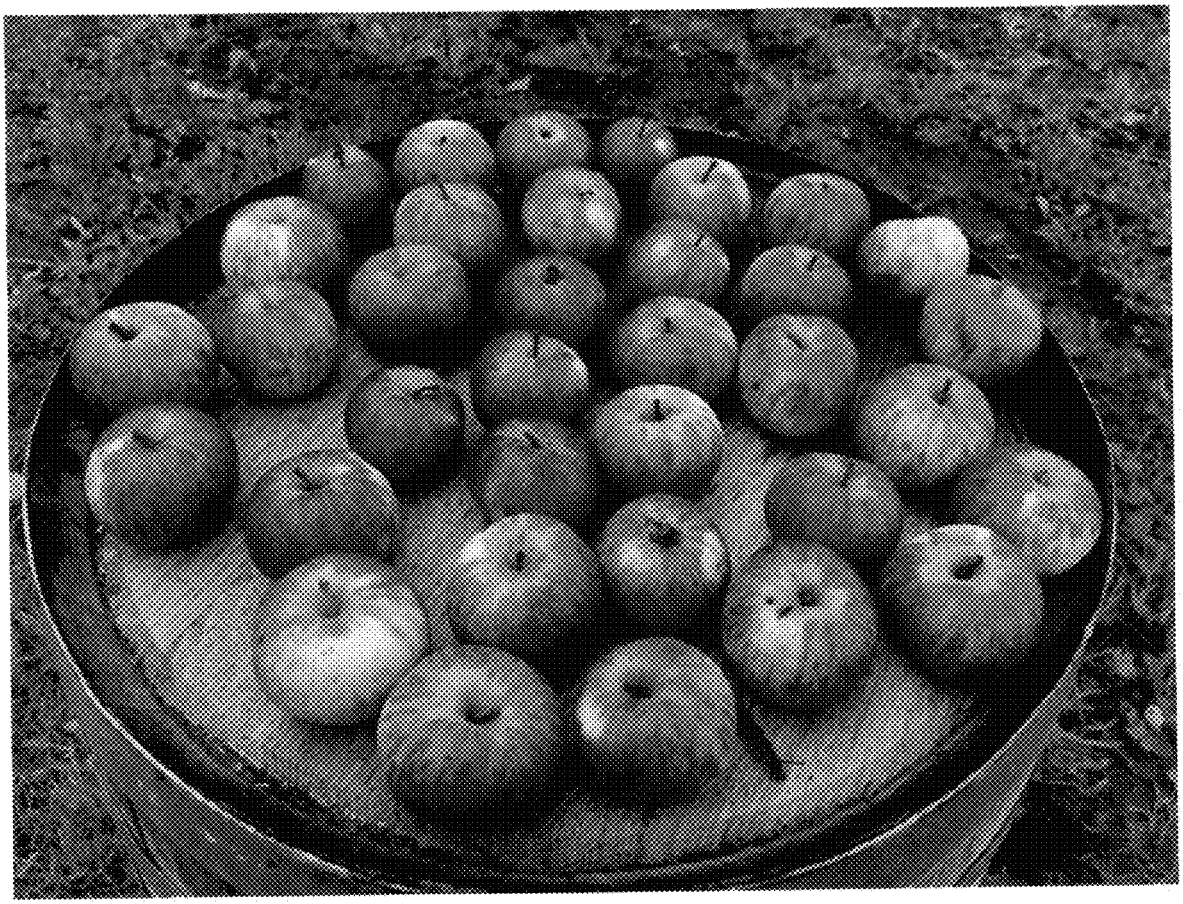
FIG. 2 is a photograph of apples from a 'J. Lincoln' apple tree.
Figure 3:
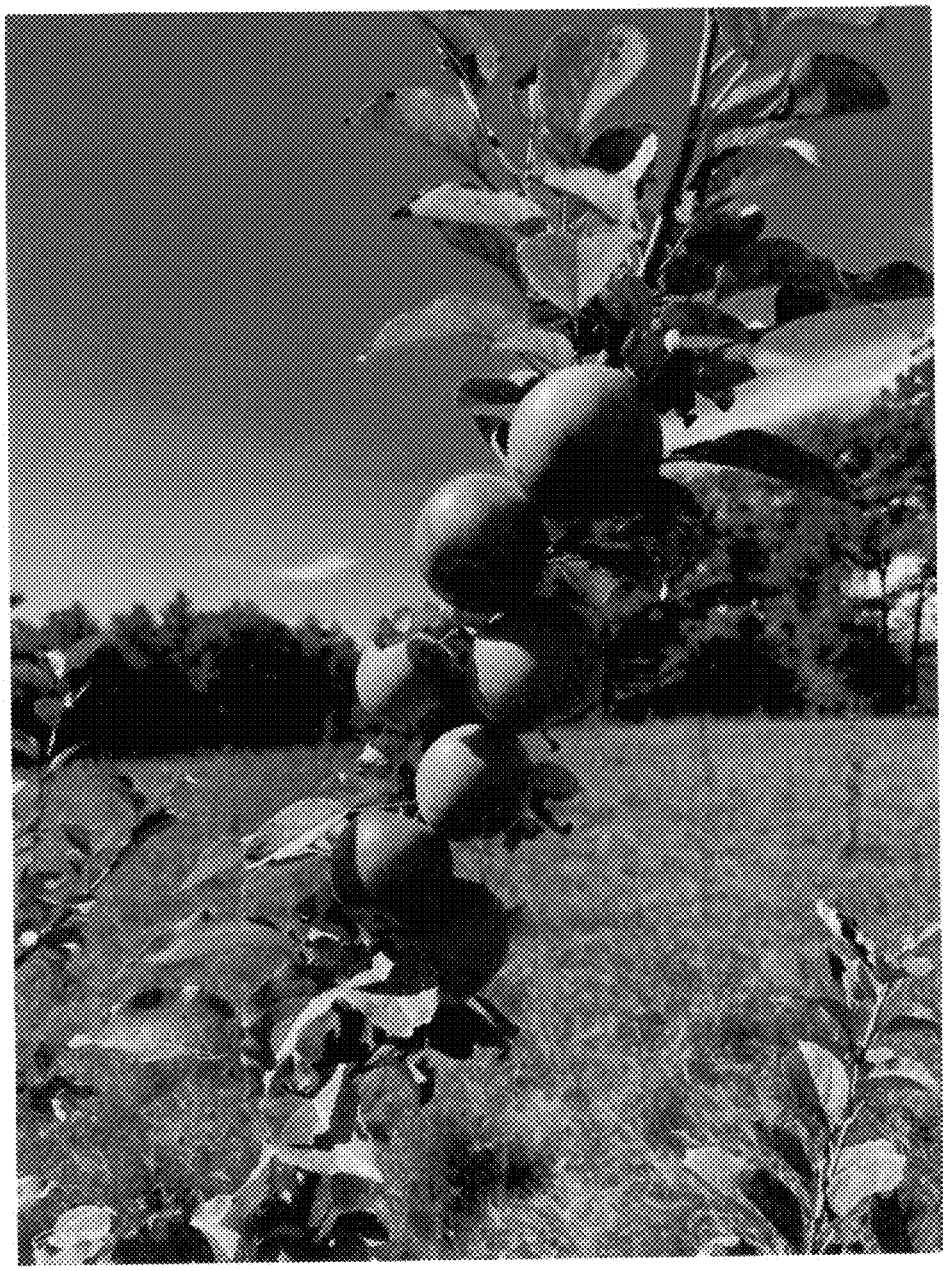
FIG. 3 is a photograph of apples on a branch of a 'J. Lincoln' apple tree.
Figure 4:
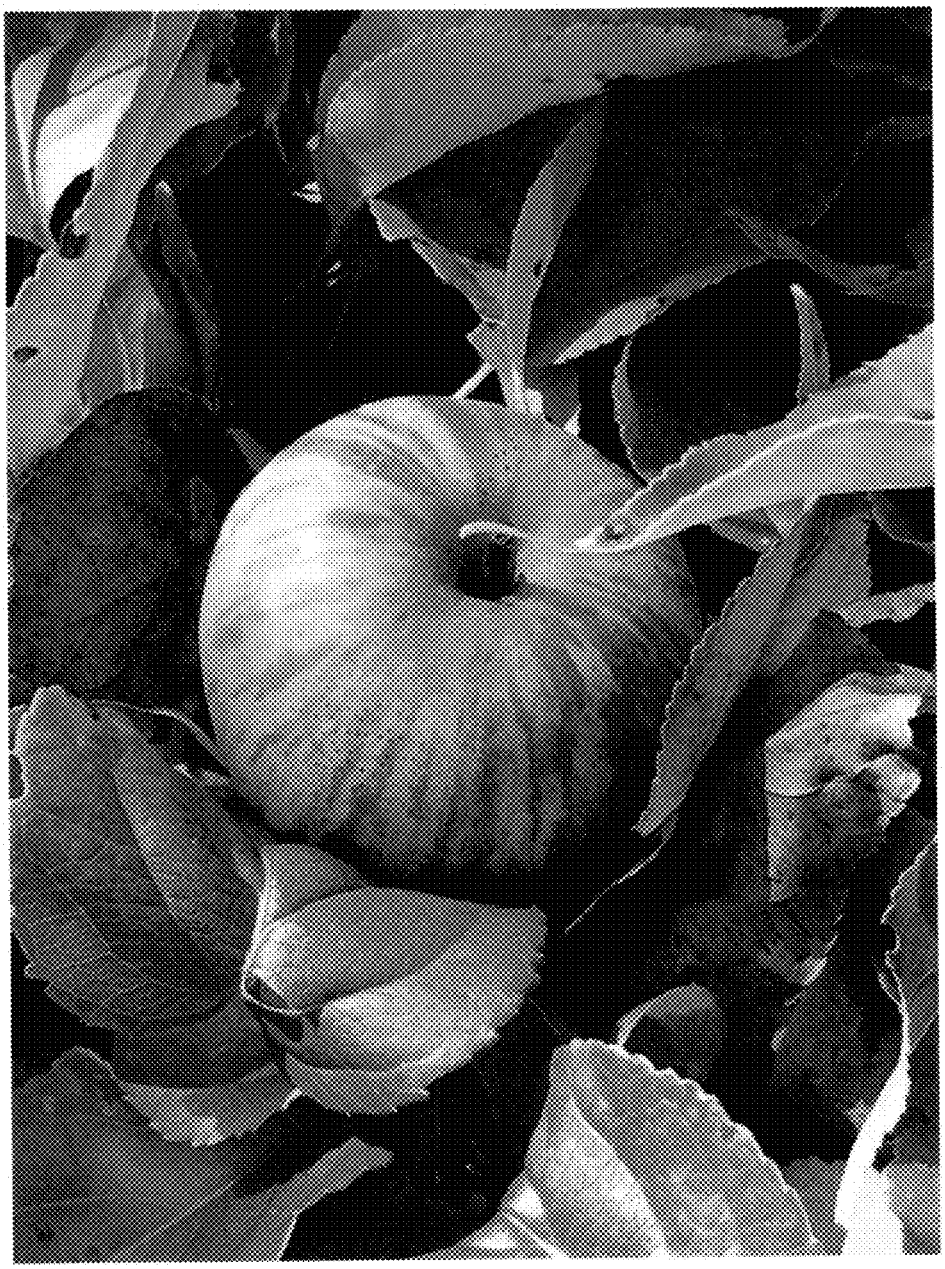
FIG. 4 is a detailed photograph of an apple from a 'J. Lincoln' apple tree.
Figure 5:
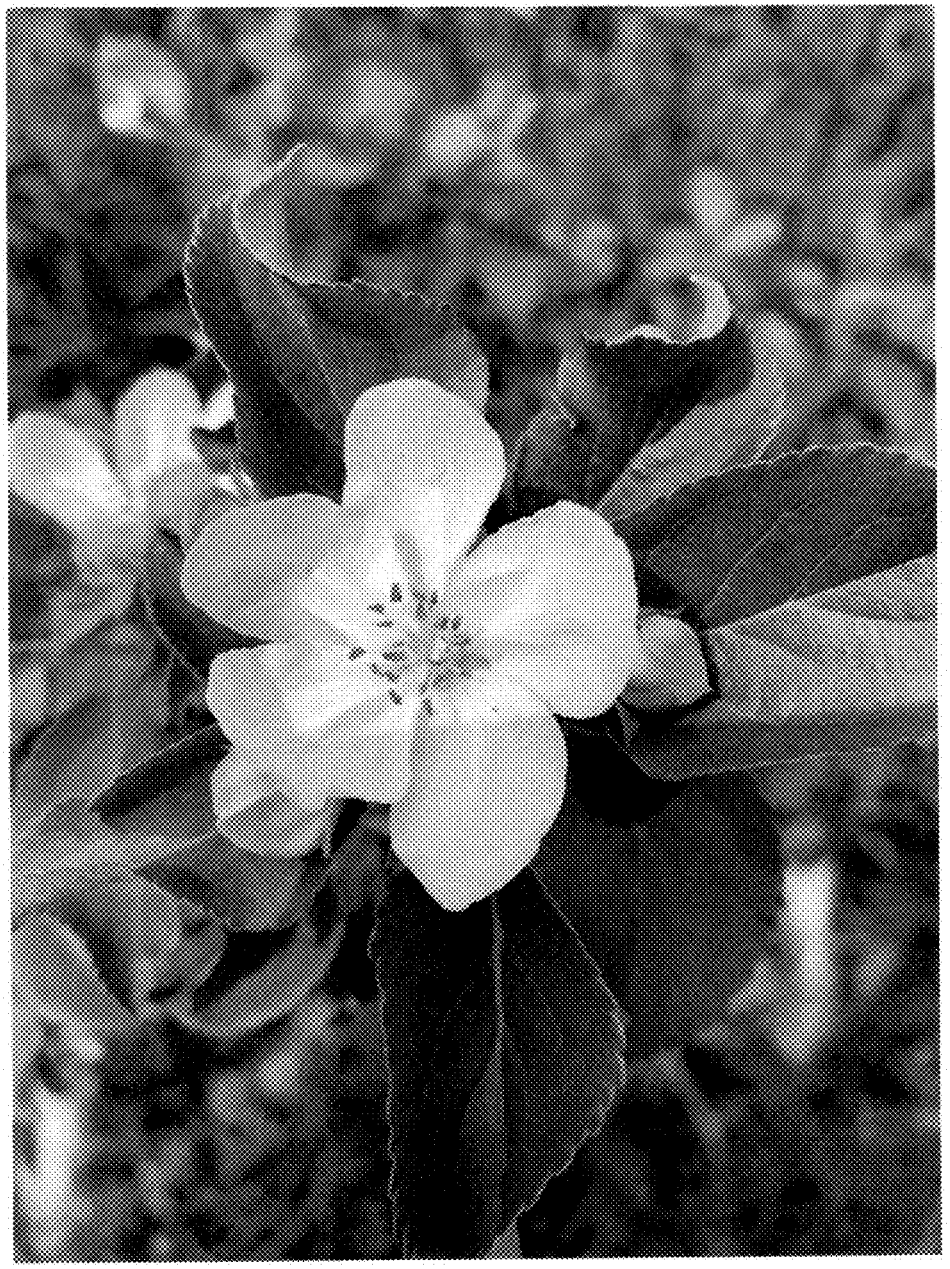
FIG. 5 is a photograph of a blossom of a 'J. Lincoln' apple tree.

Color references are made to The Royal Horticultural Society Colour Chart ($6^{th}$ Ed. 2015, reprinted 2019). The characteristics described will vary somewhat, depending upon cultural practices and climatic conditions, as well as with location and season. Quantified measurements are expressed as an average of a number of measurements taken from the described plant. The measurements of any individual plant or any group of plants of the new variety may vary from the stated average.

The following detailed botanical description was recorded in Cornish, Maine USA during the 2021 growing season. The trees were planted in 2018 and grown on Bud-118 rootstock (not patented).

Disease resistance/susceptibility: Resistant to fire blight (*Erwinia amylovora*), mildly susceptible to apple scab (*Venturia inaequalis*). The variety is cold-hardy to at least zone 4b/5a.

Tree:
- *Vigor*.—Moderate.
- *Type*.—Free standing, ramified.
- *Habit*.—Spreading.
- *Bearing*.—On shoots and spurs.
- *Age*.—5 years.
- *Size*.—8 feet tall.
- *Spread of mature tree*.—51 inches.

Trunk:
- *Reference tree diameter*.—At 2 feet above the ground: 1.25 inches.
- *Bark color*.—Greenish gray 152A.
- *Bark texture*.—Medium smooth when young, rough and shaggy on older original tree.
- *Lenticel length*.—0.04-0.12 inches.
- *Lenticel width*.—0.04 inches.
- *Lenticel shape*.—Oblong.
- *Lenticel color*.—157B.
- *Lenticel density*.—12 per square inch.

Branches (fruiting branches sized approximately 0.625 inches at 40 inches above graft union):
- *Branch characteristics*.—Typically thin to medium with frequent fruit spurs on second year wood.
- 3 *year old*.—0.75 inches in diameter, branch angle 80°; Color 177B.
- 2 *year old*.—0.5 inches in diameter, branch angle 75°; Color 177B.
- 1 *year old*.—0.25 inches in diameter, branch angle 80°; Color 201C.

Leaves:
- *Length*.—2.56-3.35 inches.
- *Width*.—1.4-1.7 inches.
- *Texture*.—Leathery.
- *Color*.—The top of the leaf is green 137B with orange/copper 152C around the edges, occurring in May. The bottom of the leaf is green 138B.
- *Form*.—Ovate.
- *Apex*.—Acute.
- *Adaxial surface pubescence*.—None.
- *Abaxial pubescence*.—Finely pubescent.
- *Margin*.—Serrate.
- *Petiole color*.—149A.
- *Petiole length*.—0.8-1.2 inches.
- *Petiole width*.—0.08-0.12 inches.

Leaf buds:
- *Length*.—0.2-0.28 inches.
- *Width*.—0.12-0.24 inches.
- *Placement on Branch*.—Alternate.
- *Intermode distance*.—0.8-1.2 inches.
- *Color*.—Greyed-purple 187A.

*Spurs*: Present on 2 yr and older wood.
- *Length*.—Varies from 0.8-3.9 inches.
- *Width*.—0.2-0.31 inches.

Flowers at balloon stage:
- *Bud shape*.—Ovate.
- *Quantity per spur*.—0.12-0.2 inches.
- *Average size*.—0.47 inches long.
- *Pedicel*.—Length 0.8-1 inch; width 0.2-0.28 inches.
- *Bloom*.—Mid/late season, similar to Macoun, typically mid-May in Cornish, Maine.
- *Sepals*.—5 sepals, color 138B on both sides, 0.2-0.28 inches in length, 0.12-0.16 inches in width, wide at the base and tapering to a point.

Blossom (1.2-1.6 inches):
- *Petals*.—5 per flower.
- *Petal shape*.—Ovate.
- *Petal length*.—0.9 inches.
- *Petal width*.—0.7 inches.
- *Petal apex shape*.—Obtuse.
- *Petal base shape*.—Rounded to slightly cordate.
- *Petal texture*.—Smooth to rugulose.
- *Petal color*.—White (NN155D) with a trace of 48C on both sides.

Pistils:
- *Length*.—0.35 inches.
- *Quantity*.—About 4 to 6 per flower.
- *Color*.—Green-white 157C with yellow-green 144C near the stigma.

Stigma:
- *Diameter*.—0.08 inches.
- *Color*.—Yellow-green 144C.

Style:
- *Diameter*.—0.028 inches.
- *Color*.—Yellow-green 144C.

Ovary:
- *Length*.—0.15 inches.
- *Diameter*.—0.05 inches.
- *Color*.—Yellow-green 144C.

Stamens:
- *Quantity*.—20.
- *Filament length*.—0.31-0.47 inches.
- *Anther diameter*.—0.04 inches.
- *Anther color*.—Yellow 10B.
- *Pollen color*.—Yellow 10B.

Fruit:
- *Size*.—Uniform.
- *Axial diameter*.—2.5 inches.
- *Transverse diameter*.—3 inches.
- *Form*.—Round-oblate, quite symmetrical and evenly proportioned.
- *Skin*.—Thin yet strong, smooth and polished.
- *Color*.—Flushes of deep vivid red 44A-53A striping over a pale yellow base 10D. Yellow Orange russet 152D radiating from the stem usually not advancing past the shoulder of the fruit.
- *Fruit flesh color*.—155B.
- *Stem*.—Medium thick, curved, average length of 0.75 inches and average width of 0.12-0.16 mm.
- *Cavity*.—Acuminate, somewhat narrow.
- *Basin*.—Obtuse with a smooth rim.
- *Calyx*.—Closed, lobes flat convergent.

Seeds:
- *Quantity per fruit*.—10.
- *Length*.—0.28 inches.
- *Width*.—0.24 inches.
- *Shape*.—Slightly elongated ovate.
- *Color*.—Brown 200B.

Use: Hard cider production.

Flavor in hard cider: Has flavors reminiscent of cherry and wild grape.

Harvest date range: Last week of September to first week of October in Cornish, Maine.

What is claimed is:

1. A new and distinct apple tree variety named 'J. Lincoln', as illustrated and described herein.

* * * * *